United States Patent [19]

Neiss et al.

[11] Patent Number: 4,625,034

[45] Date of Patent: Nov. 25, 1986

[54] 1,2-DIHYDRO; 1,2,3,4-TETRAHYDRO; 5,8 DIHYDRO; AND 5,6,7,8-TETRAHYDROQUINOLINE DERIVATIVES

[75] Inventors: Edward S. Neiss, New Canaan, Conn.; Rohit M. Desai, Millwood; Raymond D. Youssefyeh, Tarrytown, both of N.Y.

[73] Assignee: USV Pharmaceutical Corp., Fort Washington, Pa.

[21] Appl. No.: 697,999

[22] Filed: Feb. 4, 1985

[51] Int. Cl.$^4$ .................. C07D 215/14; C07D 215/20
[52] U.S. Cl. ...................................... 546/152; 546/153; 546/155; 546/157; 546/158
[58] Field of Search .............. 546/152, 153, 155, 157, 546/158

[56] References Cited

U.S. PATENT DOCUMENTS

| | | | |
|---|---|---|---|
| 4,236,912 | 12/1980 | Johnston | 546/155 |
| 4,408,076 | 10/1983 | Lee | 546/157 |
| 4,444,584 | 4/1984 | Serban | 546/155 |
| 4,563,526 | 1/1986 | Dewhirst | 546/152 |
| 4,567,184 | 1/1986 | Musser, II | 546/152 |
| 4,576,949 | 3/1986 | Smith | 546/152 |

FOREIGN PATENT DOCUMENTS 0110405 6/1984 European Pat. Off. .

Primary Examiner—Sam Rosen
Assistant Examiner—Robert Benson

[57] ABSTRACT

This invention relates to novel lipoxygenase inhibitors possessing anti-inflammatory and anti-allergic activities. The present new compounds are di- and tetra-hydroquinoline or di- and tetra-hydronapthalene derivatives, more particularly, 1,2-, 1,4-, 5,6-, or 7,8-dihydro; 1,2,3,4-tetrahydro-; 5,8-dihydro-; or 5,6,7,8-tetrahydroquinoline or napthalene derivatives of a compound of the formula:

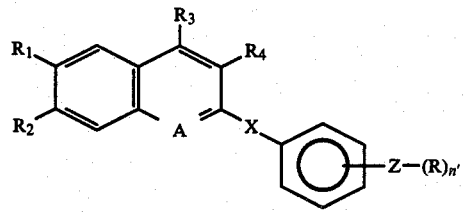

and oxides, quaternary ammonium salts and acid salts thereof; wherein
A is CH or N;
Z is an alkylene chain containing up to 10 carbon atoms in the principal chain and a total of up to 12 carbon atoms and the said alkylene chain may be attached to the phenyl group through an oxygen atom;
R is the substituent $OR_6$ attached to one of the carbon atoms of Z in which $R_6$ is H, lower alkyl or phenyl;
X is $—O(CHR_5)_m—$, alkylene of up to 2 carbon atoms in the principal chain and up to a total of 4 carbon atoms or

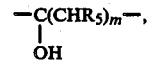

wherein
$R_5$ is H or $CH_3$;
$R_1$, $R_2$, $R_3$ and $R_4$ are each H or OH;
$n'=1$ or 2; and
$m=1$ or 2.

23 Claims, No Drawings

1,2-DIHYDRO; 1,2,3,4-TETRAHYDRO; 5,8 DIHYDRO; AND 5,6,7,8-TETRAHYDROQUINOLINE DERIVATIVES

This invention relates to new chemical compounds possessing valuable pharmaceutical activity. More particularly, the invention relates to novel lipoxygenase inhibitors possessing anti-inflammatory and anti-allergic activities.

The present new compounds are di- and tetrahydroquinoline or di- and tetra-hydro napthalene derivatives, more particularly, 1, 2-, 1, 4-, 5, 6-, or 7-, 8-dihydro-; 1, 2, 3, 4-tetrahydro-; 5, 8-dihydro; or 5, 6, 7, 8-tetrahydroquinoline or napthalene derivatives of a compound of the formula

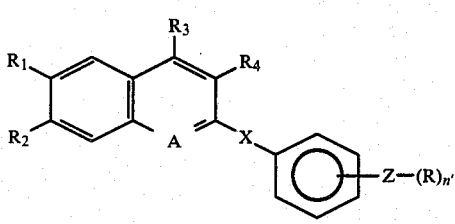

and oxides, quaternary ammonium salts and acid salts therof;
wherein
A is CH or N;
Z is an alkylene chain containing up to 10 carbon atoms in the principal chain and a total of up to 12 carbon atoms and the said alkylene chain may be attached to the phenyl group through an oxygen atom;
R is the substituent $OR_6$ attached to one of the carbon atoms of Z in which $R_6$ is H, lower alkyl or phenyl;
X is $-O(CHR_5)_m-$, alkylene of up to 2 carbon atoms in the principal chain and up to a total of 4 carbon atoms or

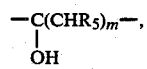

wherein
$R_5$ is H or $CH_3$;
$R_1$, $R_2$, $R_3$ and $R_4$ are each H or OH;
$n' = 1$ or 2; and
$m = 1$ or 2.

The preferred compounds are those in which X is $-CH_2O-$, wherein the oxygen is attached directly to the phenyl ring. Of these, the preferred are those compounds in which the substituent $-Z(R)_{n'}-$ is in the meta-position of the phenyl ring to which it is attached. Most preferred compounds include those in which R is OH and of these, where the OH is a secondary alcohol OH, particularly where the OH is attached to the same carbon of Z which is directly attached to the phenyl ring of the aforesaid formula.

The alkylene chains representative of Z can be normal or branched chains in which the branches are preferably methyl or ethyl and include those in which two such groups, e.g., methyl, are on the same carbon atom. The alkylene chains preferably contain up to 8 carbon atoms, wnether branched or normal chains.

Each of $R_1$, $R_2$, $R_3$ and $R_4$ may also be lower alkyl or alkoxy or other substituents which are nonreactive under the preparative procedures described herein. The phenyl group of formula I may be substituted with such groups as lower alkyl or alkoxy and hydroxy as well as other substituents which are unreactive under the aforesaid preparative procedures. Of course, where lithium or lithium compounds are employed as described hereinafter, halogen substituents should be avoided since they tend to react with the lithium reagent.

The compounds of formula I herein are also new compounds possesing lipoxygenase inhibitory activity as well as anti-inflammatory and anti-allergic activities and are described in commonly assigned copending application Ser. No. 445,876, filed Dec. 1, 1982, the disclosure of which is incorporated herein by reference for the preparation of the starting quinoline compounds employed in producing the new dihydro- and tetrahydroquinoline compounds of the present invention.

The present new compounds are prepared by art-recognized procedures by partial reduction of the corresponding quinoline or napthalene compounds of Formula I herein. For example, reaction of the corresponding quinoline or napthalene compound with diisobutylaluminum hydride according to the method described in Ann. 618 90 (1958) provides the corresponding 1, 2-dihydroquinoline or 1, 2-dihydronapthalene compounds. Reaction of the same quinoline or napthalene compounds with lithium metal and alcohol by the method described in J. Org. Chem. 36 279 (1971) provides the 5,8-dihydroquinoline or 5,8-dihydronapthalene compounds.

1,2,3,4-Tetrahydroquinoline or 1,2,3,4-tetrahydronapthalene compounds are prepared by catalytic reduction of the corresponding 1,2-dihydroquinoline or 1, 2-dihydronapthalene compounds using, for example, hydrogen over a platinum catalyst. 5,6,7,8-Tetrahydroquinoline or 5,6,7,8-tetrahydronapthalene compounds are obtained similarly from the corresponding 5,8-dihydroquinoline or 5,8-dihydronapthalene compounds, respectively.

A further method of converting the dihydroquinoline or dihydronapthalene compounds to tetrahydroquinolines or tetrahydronapthalenes involves oxidation with osmium tetroxide ($OsO_4$) to produce the corresponding 3,4-diol in the case of the 1,2-dihydroquinolines and 1,2-dihydronaphthalenes and the corresponding 6,7-diol in the case of the 5,8-dihydroquinolines and 5,8-dihydronapthalenes. In these cases, the resulting compounds are those in which $R_1$ and $R_2$ are hydroxy or $R_3$ and $R_4$ are hydroxy. To produce compounds in which $R_1$, $R_2$, $R_3$ and $R_4$ are independently hydroxy, the starting quinoline or napthalene compounds can be appropriately substituted with hydroxy groups in the desired position.

The starting compounds for the aforesaid reactions are the corresponding quinoline or napthalene compounds. Such compounds should not contain substitutes which are reactive under the aforesaid reaction conditions since it is undesirable to entertain competing reactions which could lead to mixtures of products.

The reduced products are separated from the reaction mixtures after reaction is completed or substantially completed by standard methods. Purification as well as separation of the desired products can be effected using chromatographic techniques.

The present compounds form salts with acids and the salts are especially advantageous for pharmaceutical formulations, particularly where increased water solubility of the active ingredient is desired. Of course, only pharmaceutically-acceptable acids should be employed for this purpose. Salts with acids other than pharmceutically acceptable acids are also useful for the purification and isolation of the present new compounds. Exemplary acid salts include those formed with hydrochloric, sulfuric, nitric, perchloric, malic, tartaric, malonic, citric, benzenesulfonic, toluenesulfonic and similar such acids as are known to those skilled in the art.

The compounds of the present invention can be administered to the host in a variety of forms adapted to the chosen route of administration, i.e., orally, intraveneously, intramuscularly or subcutaneous routes.

The active compound may be orally administed, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

1,2-Dihydro-2-(3-(1-hydroxyhexyl)phenyl)oxymethyl)-quinoline

A 1.0 M solution of diisobutylaluminum hydride (225 ml), 0.225 mol) is heated to 60° in an oil bath under nitrogen. To this is added with vigorous mechanical stirring, 30 g (0.09 mol) of 2-(3-(1-hydroxyhexyl)-phenoxy)methylquinoline in small portions. After completion of the addition, the reaction mixture is maintained at 65°–70° for one hour. It is then cooled in ice, carefully decomposed with a minimum amount of water, and made strongly basic with 50% NaOH. The organic layer is decanted, concentrated, and chromatographed on silica gel to give the desired amine.

EXAMPLE 2

2-(3-(1-Hydroxyhexyl)phenoxy)methyl-1,2,3,4-tetrahydroquinoline-3,4-diol

To a solution of 6.7 g (20 ml) of the above secondary amine in 100 ml, $CH_2Cl_2$ is added dropwise a solution of 5 g (35 mmol) ethyl trifluoroacetate in 25 ml $CH_2Cl_2$. The mixture is then stirred at room temperature for one hour, refluxed for 15 min., cooled, and concentrated in vacuo.

The crude trifluoroacetamide is dissolved in 50 ml t-butanol and 3.5 g (76 mmol) of N-methylmorpholine-N-oxide monohydrate is added. The solution is cooled to about 15° in an ice bath and 2.0 ml of osmium tetroxide (2.5% in t-butanol, 0.2 mmol) is added. The mixture is allowed to reach room temperature, then stirred there overnight. One gram of $Na_2S_2O_4$ is added, followed after 15 min. by 25 ml. of 2N NaOH. When TLC indicates hydrolysis of the amide, the solution is diluted with water and exhaustively extracted with chloroform. The extracts are washed once with water, dried, concentrated, and chromatographed to give the desired triol.

EXAMPLE 3

5,8-Dihydro-2-(3-(1-hydroxy-2-methylhexyl)phenoxy)-methyl quinoline

A solution of 3.5 g (10 mmol) of 2-(3-(1-hydroxy-2-methylhexyl)phenoxy methyl) quinoline in 15 ml MeOH is added dropwise to 100 ml refluxing $NH_3$. A total of 0.28 g (40 mmol) of lithium wire is then added at a rate sufficient to maintain a slight coloration. Upon completion of the addition, 10 g solid $NH_3Cl$ is added and the ammonia evaporated. Methanol-soluble products are then subjected to careful silica gel chromatography to give the desired olefin.

EXAMPLE 4

1,2,3,4-Tetrahydro-2-(3-(1-hydroxyhexyl)phenoxy)methylquinoline

The crude reduction product of Ex. 1 is dissolved in acetic acid and reduced with hydrogen over platinum catalyst. When hydrogen absorbtion is complete, the catalyst is filtered off and the filtrate is evaporated to give the title compound.

EXAMPLE 5

2-(3-(1-Hydroxyhexyl)phenoxy)methyl-5,6,7,8-tetrahydroquinoline-6,7-diol 2-(3-(1-Hydroxyhexyl)phenoxy)methylquinoline is reduced by Li/MeOH in ammonia as in Example 3. The crude product is then oxidized with $OsO_4$ as in Example 2. Chromatography of the product gives the title compound.

EXAMPLE 6

2-(3-(1-Hydroxyhexyl)phenoxy)methyl-5,6,7,8-tetrahydroquinoline

The intermediate 5,8-dihydroquinoline derivative from Example 5 is dissolved in ethanol and hydrogenated over platinum catalyst. Hydrogen uptake is monitored and the reaction stopped when exactly one equivalent of hydrogen is absorbed. The catalyst is removed by filtration and the filtrate concentrated and chromatographed to give the title compound.

EXAMPLE 7

2-(Hydroxymethyl)-1,2,3,4-tetrahydronaphthalene

To a solution of 5.0 g (0.028 mol) 1,2,3,4-tetrahydro-2-naphthoic acid in 30 ml of dry tetrahydrofuran, 1.1 g (0.029 mol) lithium aluminum hydride was added over a period of one half hour. After the addition was completed, the mixture was stirred at room temperature for a period of 2 hours. It was then cooled on ice, and was carefully decomposed with a minimum amount of saturated $Na_2SO_4$ solution. The reaction mixture was filtered and washed with ether. The organic layer was combined and extracted with water. Concentration of the dried organic layer yielded 4.4 g of crude product.

EXAMPLE 8

2-(Methylsulfonyloxy)methyl-1,2,3,4-tetrahydronaphthalane 6.1 g (0.05 mol) of methylsulfonyl chloride was added dropwise, over a period of one half hour to a solution of 4.3 g (0.026 mol) 2-(hydroxymethyl)-1,2,3,4-tetrahydronaphthalene in 15 ml pyridine. After the addition, the reaction mixture was stirred at room temperature for 1 hour and then it was poured over crushed ice containing 20 ml concentrated hydrochloride acid. A gummy solid separated, which solidified upon stirring. This solid was filtered, washed with water and suction dried to give 6 g of the desired compound. This crude product was used in the next step without further purification.

EXAMPLE 9

2-(Iodomethyl)-1,2,3,4-tetrahydronaphthalane

A mixture of 6.0 g of crude 2-(methylsulfonyloxy)-methyl-1,2,3,4-tetrahydronaphthalene, 12.5 g (0.075 ml) KI and 5 drops of concentrated HCl in 100 ml acetone was refluxed for 2 hours. The reaction mixture was poured onto crushed ice containing $Na_2SO_3$. A brownish oil separated which was extracted with ether. The extract was washed with dilute $Na_2SO_3$ and then with water, dried over $MgSO_4$ and concentrated to dryness under reduced pressure to obtain a light yellow solid (4.9 g).

EXAMPLE 10

2-[3-(1-Hydroxyhexyl)phenoxymethyl]-1,2,3,4-tetrahydronaphthalane

A mixture of 4.0 g (0.018 mol) 2-(iodomethyl)-1,2,3,4-tetrahydronaphthalene, 3.4 g (0.018 mol) 3-(1-hydroxyhexyl)phenol and 3.4 ml NaOH (5N) in 50 ml DMSO and 20 ml THF was stirred at room temperature for a period of 48 hours. The reaction mixture was concentrated under reduced pressure. The concentrated reaction mixture was poured into water and extracted with ether. The ether extract was washed with water, dried over $MgSO_4$ and concentrated to dryness under reduced pressure. The residue was passed through a silica gel column using hexane/ethyl acetate (3:1) as eluent. Evaporation of eluent gave an oily product (1.3 g).

EXAMPLE 11

1,2-Dihydro-2-[3-(1-hydroxyhexyl)phenyloxymethyl]-naphthalene

A mixture of 1.1 g (0.004 mol) 1,2-dihydro-(2-iodomethyl)-naphthalene, 0.8 g (0.004 mol) 3-(1-hydroxyhexyl)phenyl and 4 ml NaOH (2N) in 10 ml DMSO and 25 ml THF was stirred at room temperature for a period of 48 hours. The reaction mixture was concentrated under reduced pressure. The concentrated reaction mixture was poured into water and extracted with ether. The ether extract was washed with water, dried over $MgSO_4$ and concentrated to dryness under reduced pressure. The crude product was purified by passing it through a silica gel column.

EXAMPLE 12

1,4-Dihydro-2-[3-(1-hydroxyhexyl)phenyloxymethyl]-naphthalene

A mixture of 1.1 g (0.004 mol) 1,2-dihydro(2-iodomethyl)-naphthalene, 0.8 g (0.004 mol) 3-(1-hydroxyhexyl)phenyl and 4 ml NaOH (2N) in 10 ml DMSO and 25 ml THF was stirred at room temperture for a period of 48 hours. The reaction mixture was concentrated under reduced pressure. The concentrated reaction mixture was poured into water and extracted with ether. The ether extract was washed with water, dried over MgSO$_4$ and concentrated to dryness under reduced pressure. The crude product was purified by passing it through a silica gel column.

EXAMPLE 13

2-[3-(1-Hydroxyhexyl)phenoxymethyl]quinoline methiodide

A mixture of 8.3 g (0.025 mol) 2-[3-(1-hydroxyhexyl)-phenoxymethyl]quinoline and 7 g (0.05 mol) iodomethane in 50 ml toluene was heated at 100° C. (bath temperature) in a pressure bottle for a period of 48 hours. The precipitate obtained was filtered and washed with toluene and dried to give a yellow solid (5 g).

EXAMPLE 14

N-Methyl-1,2-dihydro-2-[3-(1-hydroxyhexyl)phenoxymethyl]quinoline

To a stirred mixture of 0.2 g (0.005 mol) NaBH$_4$ in 10 ml ethanol was added 1.2 g (0.0025 mol) of 2-[3-(1-hydroxyhexyl)phenoxymethyl]quinoline methiodide in small portions. After completion of the addition, the reaction mixture was stirred at room temperature for a period of 1 hour. It was then poured into ice cold NH$_4$Cl solution and extracted with CH$_2$Cl$_2$. The CH$_2$Cl$_2$ extract was washed with water, dried over MgSO$_4$ and evaporated to dryness under reduced pressure. The crude product was purified by passing it through a silica gel column.

EXAMPLE 15

N-Methyl-2-[3-(1-hydroxyhexyl)phenoxymethyl]-1,2,3,4-tetrahydroquinoline

A mixture of 0.88 g (0.0025 mol) N-methyl-1,2,-dihydro-2-[3-(1-hydroxyhexyl)phenoxymethyl]quinoline and 0.05 g Pd/C (10%) in 100 ml ethanol was hydrogenated at 50 psi for a period of 2 hours. After filtration and evaporation of the solvent under reduced pressure, the residue was passed through a silica gel column and the desired product was isolated.

EXAMPLE 16

2-[3-(1-Hydroxyhexyl)phenoxymethyl]quinoline-N-oxide

A mixture of 5.0 g (0.015 mol) 2-[3-(1-hydroxyhexyl)-phenoxymethyl]quinoline and 3.0 g (0.017 mol) m-chloroperoxybenzoic acid in 100 ml CH$_2$Cl$_2$ was stirred at room temperature for a period of 24 hours. The reaction mixture was extracted with dilute NaHCO$_3$ solution, washed with water, dried over MgSO$_4$ and concentrated to dryness under reduced pressure. The residue was triturated with large amounts of ether to obtain a solid. This solid was filtered, washed with ether and dried to give the desired compound (2 g).

Simiarly are prepared:
2-(3-(1-hydroxy-2-methylhexyl)phenoxy)methyl-1,2,3,4-tetrahydroquinoline;
2-(3-(1-hydroxy-2,2-dimethylhexyl)phenoxy)methyl-5,8-dihydroquinoline;
2-(3-(1-hydroxy-2-methylhexyl)phenoxy)methyl-5,6,7,8-tetrahydroquinoline-6,7-diol;
2-(3-(1-hydroxy-2,2-dimethylhexyl)phenoxy)methyl-1,2-dihydroquinoline;
2-(3-(1-hydroxy-2,2-dimethylhexyl)phenoxy)methyl-1,2,3,4-tetrahydroquinoline-3,4-diol;
2-(3-(2-hydroxy-2-heptyl)phenoxy)methyl-5,8-dihydroquinoline;
2-(3-(1-hydroxy-2-methylhexyl)phenoxy)methyl-5,6,7,8-tetrahydroquinoline;
2-(3-(1-hydroxy-2,2-dimethylhexyl)phenoxy)methyl-5,6,7,8-tetrahydroquinoline-6,7-diol;
2-(3-(2-hydroxy-2-heptyl)phenoxy)methyl-1,2,3,4-tetrahydroquinoline;
2-(3-(1-hydroxy-2-phenoxyethyl)phenoxy)methyl-1,2,3,4-tetrahydroquinoline-3,4-diol;
2-(3-(1-hydroxy-2-methylhexyl)phenoxy)methyl-1,2-dihydroquinoline;
2-(3-(1-hydroxy-2-phenoxyethyl)phenoxy)methyl-5,6,7,8-tetrahydroquinoline.

The present new compounds show significant lipoxygenase inhibition and are valuable in the treatment of inflammatory conditions and allergic responses such as anaphylaxis and asthma.

What is claimed is:

1. A 1,2-dihydro; 1,2,3,4-tetrahydro; 5,8-dihydro; or 5,6,7,8-tetrahydro derivative of a compound of the formula:

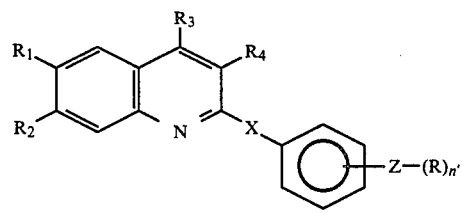

and acid salts thereof:
wherein
Z is an alkylene chain containing up to 10 carbon atoms in the principal chain and a total of up to 12 carbon atoms and the said alkylene chain may be attached to the phenyl group through an oxygen atom;

R is the substituent OR$_6$ attached to one of the carbon atoms of Z in which R$_6$ is H, lower alkyl or phenyl;

X is —O(CHR$_5$)$_m$—, alkylene of up to 2 carbon atoms in the principal chain and up to a total of 4 carbon atoms or

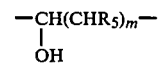

wherein
R$_5$ is H or CH$_3$;
R$_1$, R$_2$, R$_3$ and R$_4$ are each H or OH;
n' = 1 or 2; and
m = 1 or 2.

2. A 1,2-dyhyro; 1,2,3,4-tetrahydro; 5,8-dihydro or 5,6,7,8-tetrahydro derivative of a compound of the formula:

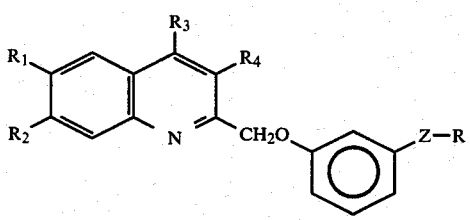

and salts thereof;
wherein
Z is an alkylene chain containing up to 10 carbon atoms in the principal chain and a total of up to 12 carbon atoms and the said alkylene chain may be attached to the phenyl group through an oxygen atom;

R is the substituent $OR_6$ attached to one of the carbon atoms of Z in which $R_6$ is H, lower alkyl or phenyl; and $R_1$, $R_2$, $R_3$ and $R_4$ are each H or OH.

3. A 1,2-dihydro; 1,2,3,4-tetrahydro; 5,8-dihydro or 5,6,7,8-tetrahydro derivative of a compound of the formula:

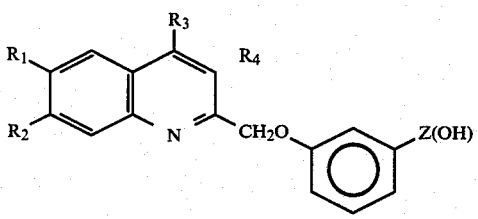

and salts thereof;
wherein
Z is an alkylene chain containing up to 10 carbon atoms in the principal chain and a total of up to 12 carbon atoms and the said alkylene chain may be attached to the phenyl group through an oxygen atom and the OH substituent is located on any one of the carbon atoms of Z; and $R_1$, $R_2$, $R_3$ and $R_4$ are each H or OH.

4. The compound according to claim 3 wherein the OH group on Z is a secondary alcohol group.

5. The compound according to claim 3 wherein the OH group on Z is attached to the carbon atom attached directly to the phenyl group.

6. The compound according to claim 3 which is 1,2-dihydro-2-(3-(1-hydroxyhexyl)phenoxy)methyl)quinoline.

7. The compound according to claim 3 which is 2-(3-(1-hydroxyhexyl)phenoxy)methyl-1,2,3,4-tetrahydroquinoline-3,4-diol.

8. The compound according to claim 3 which is 5,8-dihydro-2-(3-(1-hydroxy-2-methylhexyl)phenoxy)methylquinoline.

9. The compound according to claim 3 which is 1,2,3,4-tetrahydro-2-(3-(1-hydroxyhexyl)phenoxy)methylquinoline.

10. The compound according to claim 3 which is 2-(3-(1-hydroxyhexyl)phenoxy)methyl-5,6,7,8-tetrahydroquinoline-6,7-diol.

11. The compound according to claim 3 which is 2-(3-(1-hydroxyhexyl)phenoxy)methyl-5,6,7,8-tetrahydroquinoline.

12. The compound according to claim 3 which is 2-(3-(1-hydroxy-2-methylhexyl)phenoxy)methyl-1,2,3,4-tetrahydroquinoline.

13. The compound according to claim 3 which is 2-(3-(1-hydroxy-2,2-dimethylhexyl)phenoxy)methyl-5,8-dihydroquinoline.

14. The compound according to claim 3 which is 2-(3-(1-hydroxy-2-methylhexyl)phenoxy)methyl-5,6,7,8-tetrahydroquinoline-6,7-diol.

15. The compound according to claim 3 which is 2-(3-(1-hydroxy-2,2-dimethylhexyl)phenoxy)methyl-1,2-dihydroquinoline.

16. The compound according to claim 3 which is 2-(3-(1-hydroxy-2,2-dimethylhexyl)phenoxy)methyl-1,2,3,4-tetrahydroquinoline-3,4-diol.

17. The compound according to claim 3 which is 2-(3-(2-hydroxy-2-heptyl)phenoxy)methyl-5,8-dihydroquinoline.

18. The compound according to claim 3 which is 2-(3-(1-hydroxy-2-methylhexyl)phenoxy)methyl-5,6,7,8-tetrahydroquinoline.

19. The compound according to claim 3 which is 2-(3-(1-hydroxy-2,2-dimethylhexyl)phenoxy)methyl-5,6,7,8-tetrahydroquinoline-6,7-diol.

20. The compound according to claim 3 which is 2-(3-(2-hydroxy-2-heptyl)phenoxy)methyl-1,2,3,4-tetrahydroquinoline.

21. The compound according to claim 1 which is 2-(3-(1-hydroxy-2-phenoxyethyl)phenoxy)methyl-1,2,3,4-tetrahydroquinoline-3,4-diol.

22. The compound according to claim 3 which is 2-(3-(1-hydroxy-2-methylhexyl)phenoxy)methyl-1,2,-dihydroquinoline.

23. The compound according to claim 3 which is 2-(3-(1-hydroxy-2-phenoxyethyl)phenoxy)methyl-5,6,7,8-tetrahydroquinoline.

* * * * *